(12) United States Patent
Ohyama et al.

(10) Patent No.: US 6,872,207 B2
(45) Date of Patent: Mar. 29, 2005

(54) RESECTSCOPE APPARATUS (75) Inventors: Masahide Ohyama, Hino (JP); Kenji Harano, Hachioji (JP); Kazuya Hijii, Tama (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/437,375

(22) Filed: May 13, 2003

(65) Prior Publication Data

US 2003/0233088 A1 Dec. 18, 2003

Related U.S. Application Data (63) Continuation of application No. PCT/JP02/06039, filed on Jun. 18, 2002.

(51) Int. Cl.$^7$ ............................................... A61B 17/14
(52) U.S. Cl. ........................... 606/46; 606/41; 607/101; 607/105; 604/20; 604/22
(58) Field of Search ........................ 606/41, 42, 45–50; 607/101–105; 604/21, 22, 114

(56) References Cited

U.S. PATENT DOCUMENTS 5,843,019 A * 12/1998 Eggers et al. ................. 604/22
6,113,597 A 9/2000 Eggers et al.

FOREIGN PATENT DOCUMENTS

| JP | 4-44739 | 2/1992 |
|----|---------|--------|
| JP | 4-45694 | 10/1992 |
| JP | 2000-201946 | 7/2000 |
| JP | 2002-177298 | 6/2002 |
| WO | WO 97/00646 | 1/1997 |
| WO | WO 99/16371 | 4/1999 |

* cited by examiner

Primary Examiner—Rosiland Rollins
(74) Attorney, Agent, or Firm—Scully, Scott, Murphy & Presser (57) ABSTRACT

According to a resectscope apparatus of the present invention, in order to control the output properly by discriminating electric characteristics of perfusion fluids, under control of the control circuit (101), a predetermined detection current is fed from the output transformer circuit (105) by using power, which does not produce an electrical breakdown even in the insulative liquid (161) or in the air. A predetermined lapse of time until the output is stabilized is waited. The sensor signal processing circuit (107) A/D converts and measures current values detected by the current sensors (106a) and (106b). Whether a treating electrode and a return electrode are in a conductive liquid, in an insulative liquid or in the air is determined. Then, the output control processing is performed.

14 Claims, 9 Drawing Sheets

RESECTSCOPE APPARATUS

CROSS REFEERENCE TO RELATED APPLICATION

This application is a continuation of PCT application no. PCT/JP02/06039 filed on Jun. 18, 2002, the entire contents of which is incorporated herein by its reference.

TECHNICAL FIELD

The present invention relates to a resectscope apparatus for electrically incising, resecting, and transpiring body tissue by using an endoscope.

BACKGROUND ART

In general, a resectscope is used for transurethral resection (TUR) and transcervical resection (TCR). The resectscope mainly includes, in a long, narrow and hollow sheath to be inserted into a body cavity, an optical scope (sometimes simply called scope), which is an endoscope for observation, and an electrode unit for resecting living body tissue.

As the resectscope, for example, Japanese Examined Utility Model Registration Application Publication No. 4-45694 discloses a resectscope apparatus an electrode for rigid scope surgical instrument having a rigid heat-resistance member between a distal end portion of an electric insulative member and an elemental wire. The rigid heat-resistance member is in contact with the periphery of the elemental wire. Thus, burns of the electric insulative member can be prevented.

When the resectscope is used for resecting the prostate, for example, D-sorbitol may be supplied which is insulating transparent liquid as a perfusion fluid for expanding the inside of a narrow cavity. Thus, the cavity is expanded, and a sheath of the resectscope can be inserted into the cavity.

Then, the surface of a lesion is observed by using a scope located within the sheath. At the same time, high frequency current passes through a treating electrode of an electrode unit located at a distal end portion opening of the sheath. By discharging, current flows from the treating electrode to an external electrode located outside of a body through the liquid filled within the cavity. Then, the operating portion is manipulated to move the treating electrode back and forth for treating the lesion.

Here, because the perfusion fluid filled within the cavity is an insulative liquid, the dispersion of current traveling from the treating electrode to the external electrode can be prevented. Thus, more efficient treatment can be performed.

However, when a treatment is performed by filling an insulative liquid within a cavity, and when the treating time is longer, the liquid is absorbed into a blood vessel, which may have bad influences on a human body. Therefore, the operation time is limited.

In order to overcome the problem, a physiological saline, which is a conductive liquid, may be filled within a cavity as a perfusion fluid. However, when the conductive liquid is filled within a cavity, current to flow from the treating electrode to the external electrode disperses through the liquid. Therefore, discharging does not occur on a lesion, which disadvantageously cannot achieve effective treatment.

Thus, Japanese Unexamined Patent Application Publication No. 2000-201946 discloses a resectscope apparatus including a treating electrode and a return electrode. The treating electrode is located in the vicinity of a long, narrow and hollow sheath distal end portion to be inserted into a body cavity filled with a conductive liquid. The treating electrode treats a body tissue by using high frequency cauterization current. The return electrode is located within the conductive liquid. The return electrode receives current from the treating electrode. An insulating portion is provided on at least a body tissue non-contact surface of the treating electrode. Thus, high frequency current supplied to the treating electrode within the cavity filled within the conductive liquid does not leak from the insulating portion on the body tissue non-contact surface of the treating electrode to the liquid. The high frequency current is efficiently discharged from a body tissue contact surface of the treating electrode in contact with a body tissue. The high frequency current flows to the return electrode.

However, in the resectscope apparatus according to Japanese Unexamined Patent Application Publication No. 2000-201946, a distance between the treating electrode and the return electrode is small. Therefore, when energized in the air or in a nonconductive liquid by mistake, excessively large voltage occurs. Then, an electrical breakdown may be produced between the electrodes disadvantageously.

The present invention was made in view of the above-described problems. It is an object of the present invention to provide a resectscope apparatus, which can properly control outputs by discriminating electrical characteristics of perfusion fluids.

DISCLOSURE OF INVENTION

In a resectscope apparatus, having two electrodes provided in a conductive solution within a body cavity and a high frequency current supply unit for supplying high frequency current between the two electrodes, the high frequency current is discharged from at least one of the two electrodes to a living tissue, and the living tissue is resected and is coagulated. The apparatus includes a comparing unit for comparing resistance values around the two electrodes with a predetermined threshold value, and a control unit for controlling an output of the high frequency current supply unit based on a comparison result by the comparing unit.

BEST MODE FOR CARRYING OUT THE INVENTION

An embodiment of the invention will be described below with reference to drawings.

Figure 1:
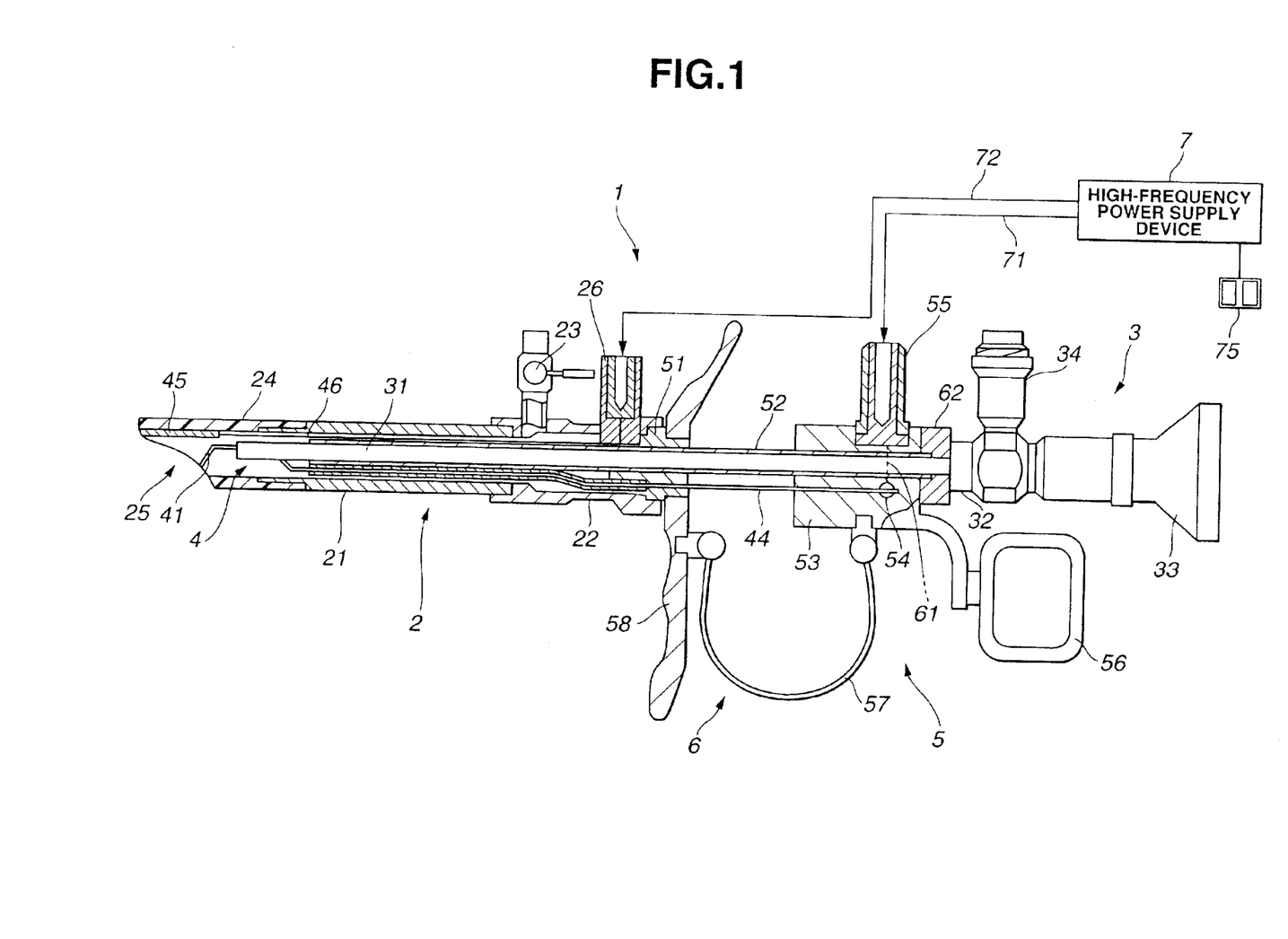
FIG. 1 is a construction diagram showing a construction of a resectscope apparatus according to an embodiment of the present invention.
Figure 2:
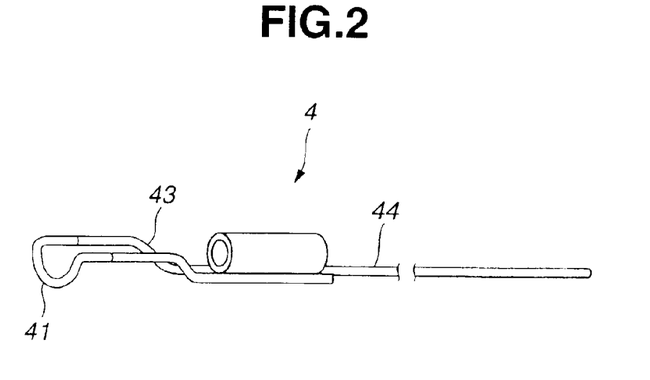
FIG. 2 is a construction diagram showing a construction of a treating electrode in FIG. 1.
Figure 3:
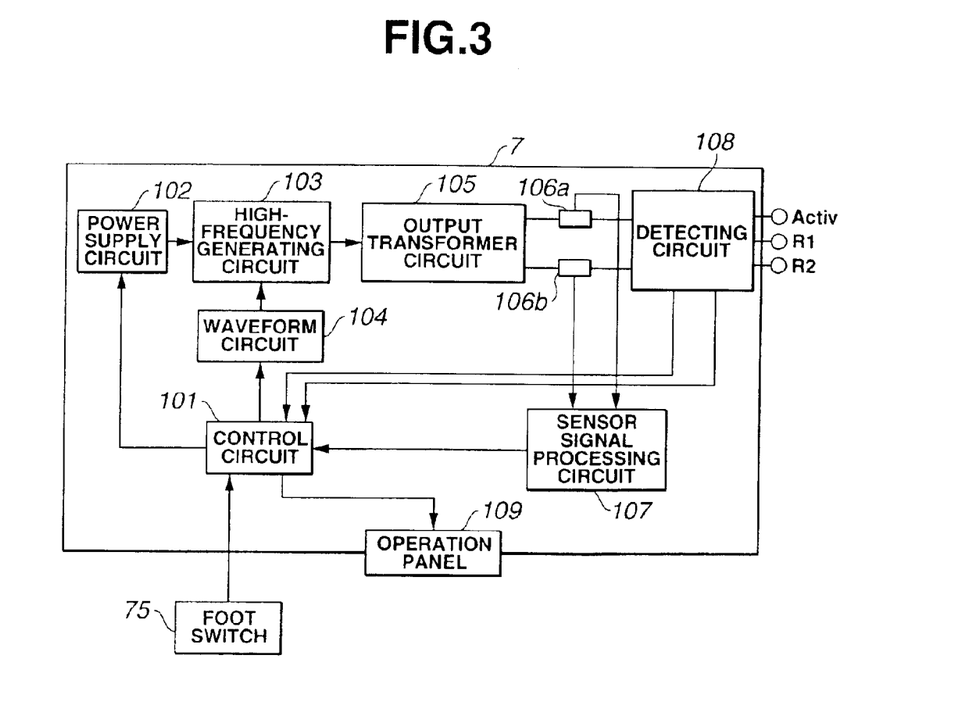
FIG. 3 is a construction diagram showing a construction of a high frequency power supply device in FIG. 1.
Figure 4:
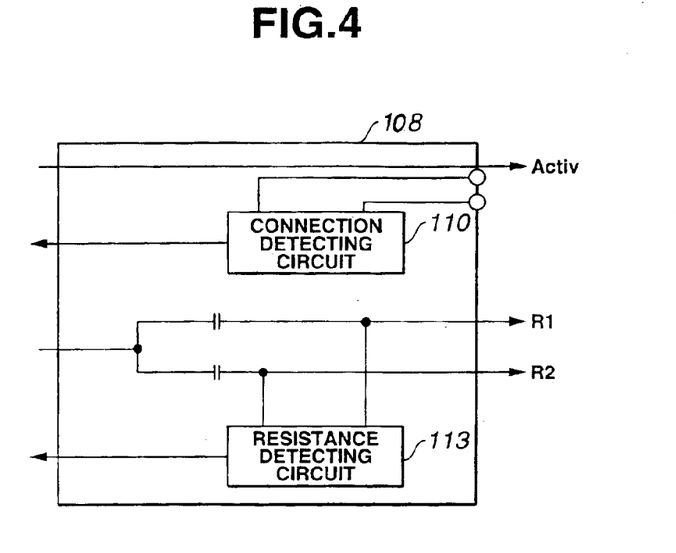
FIG. 4 is a construction diagram showing a construction of a detecting circuit in FIG. 3.
Figure 5:
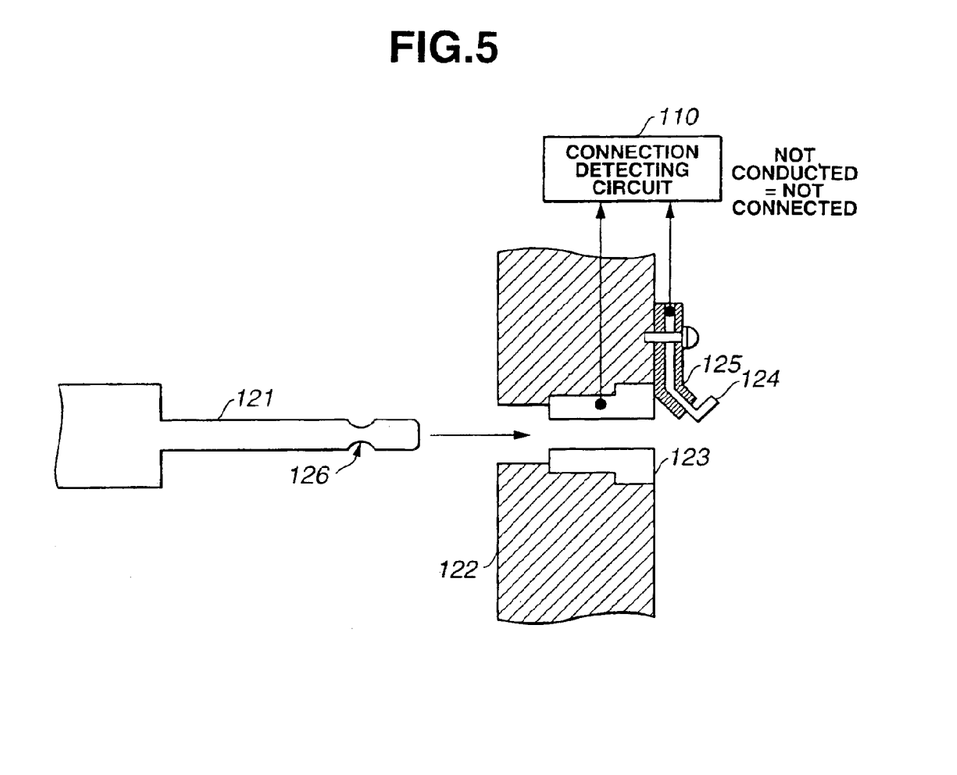
FIG. 5 is a first diagram for explaining an operation of a connection detecting circuit in FIG. 4.
Figure 6:
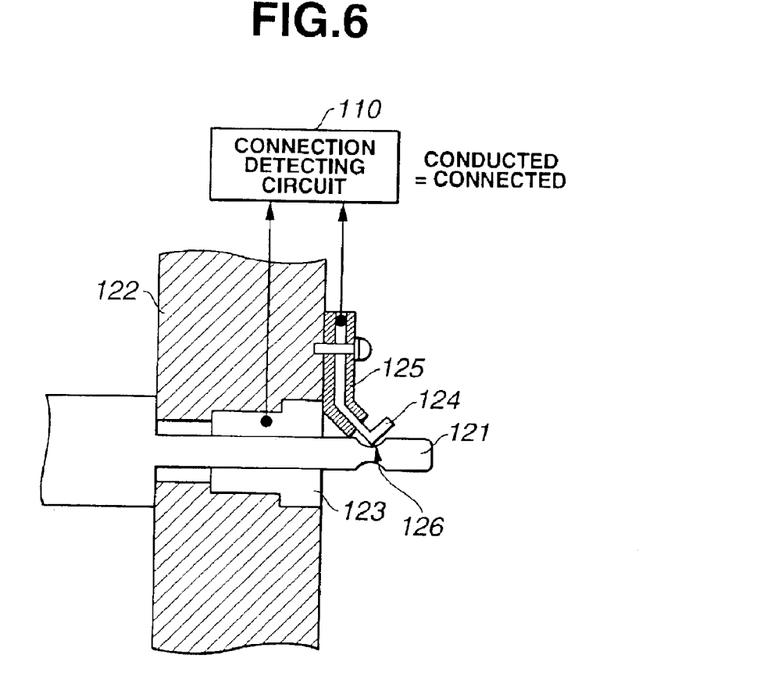
FIG. 6 is a second diagram for explaining an operation of a connection detecting circuit in FIG. 4.
Figure 7:
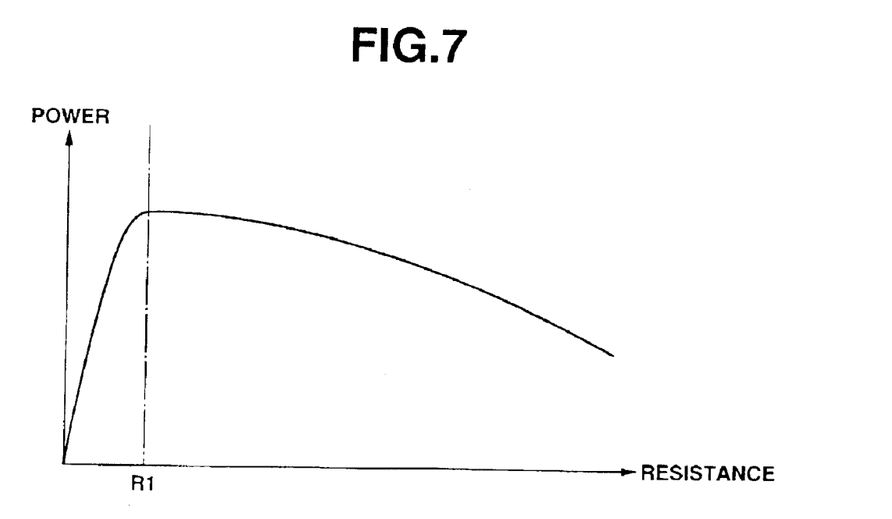
FIG. 7 is a diagram showing load characteristics of power supply in an output transformer circuit in FIG. 3.
Figure 8A:
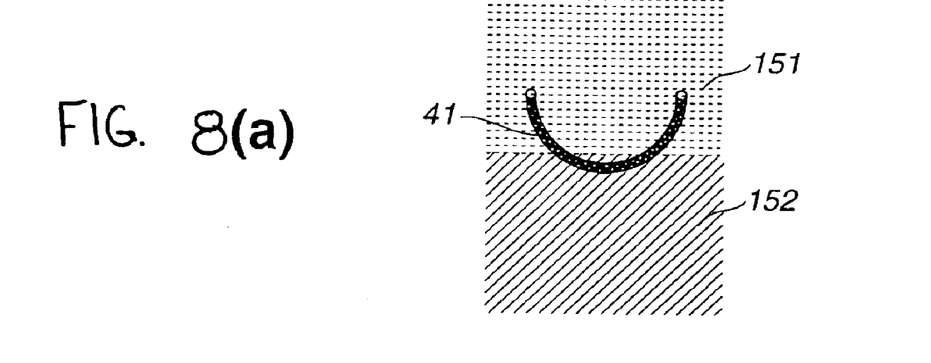
FIGS. 8(a) and 8(b) are diagrams for explaining an operation of a treating electrode by using power supplied from the output transformer circuit in FIG. 3.
Figure 8B:
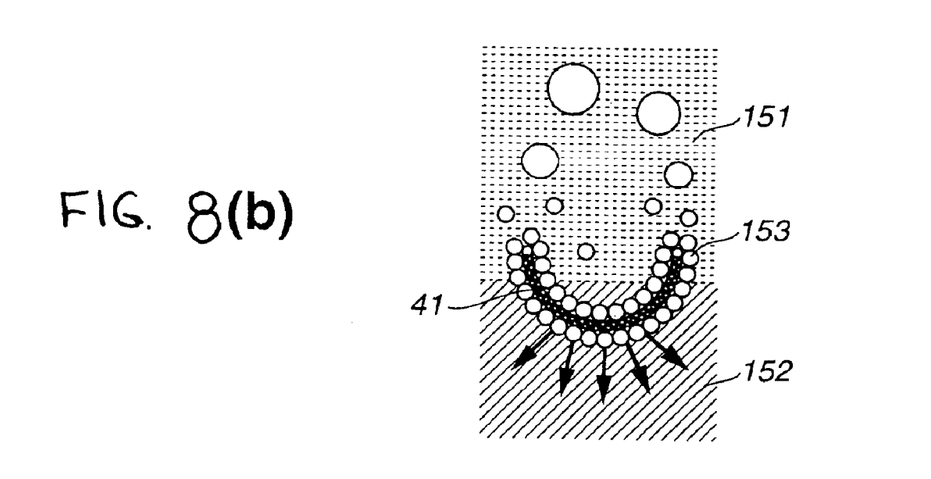
Figure 9:
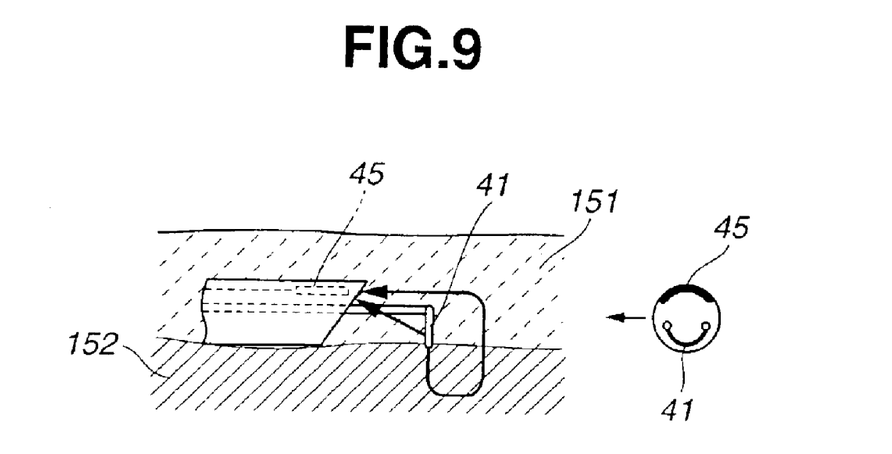
FIG. 9 is a diagram showing current flowing between a treating electrode and return electrode in FIG. 1 in a conductive liquid.
Figure 10:
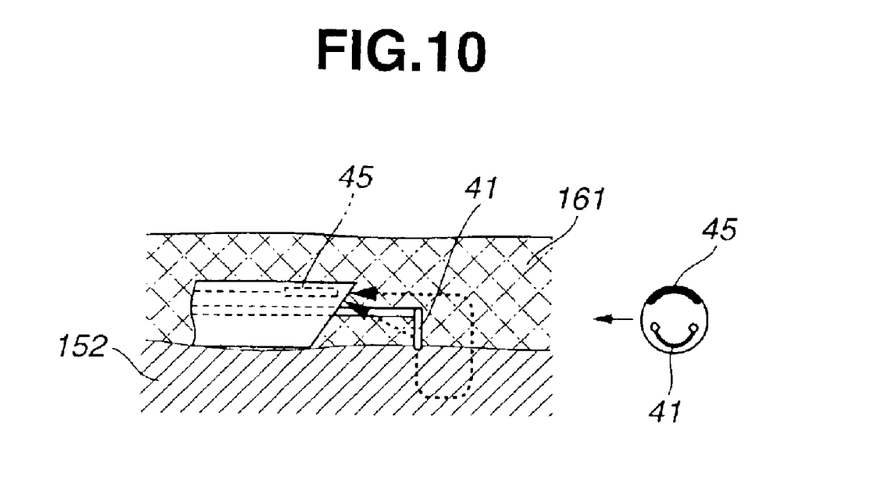
FIG. 10 is a diagram showing current flowing between the treating electrode and return electrode in FIG. 1 in an insulative liquid.
Figure 11:
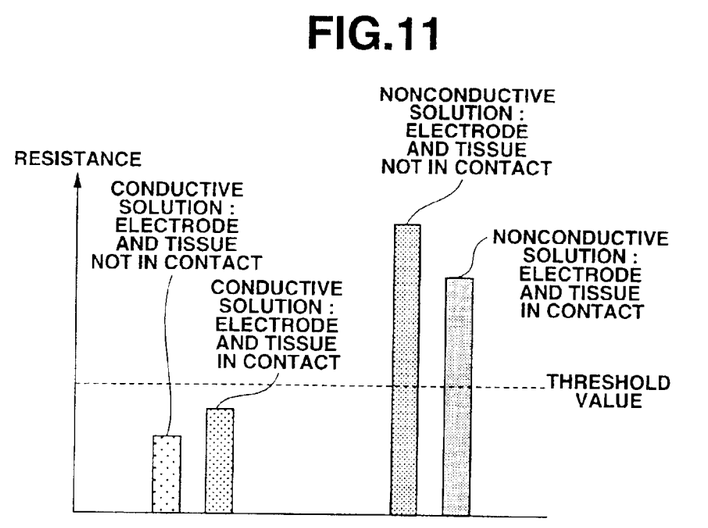
FIG. 11 is a diagram showing resistances between the treating electrode and return electrode in FIG. 1 in the conductive liquid and in the insulative liquid.
Figure 12:
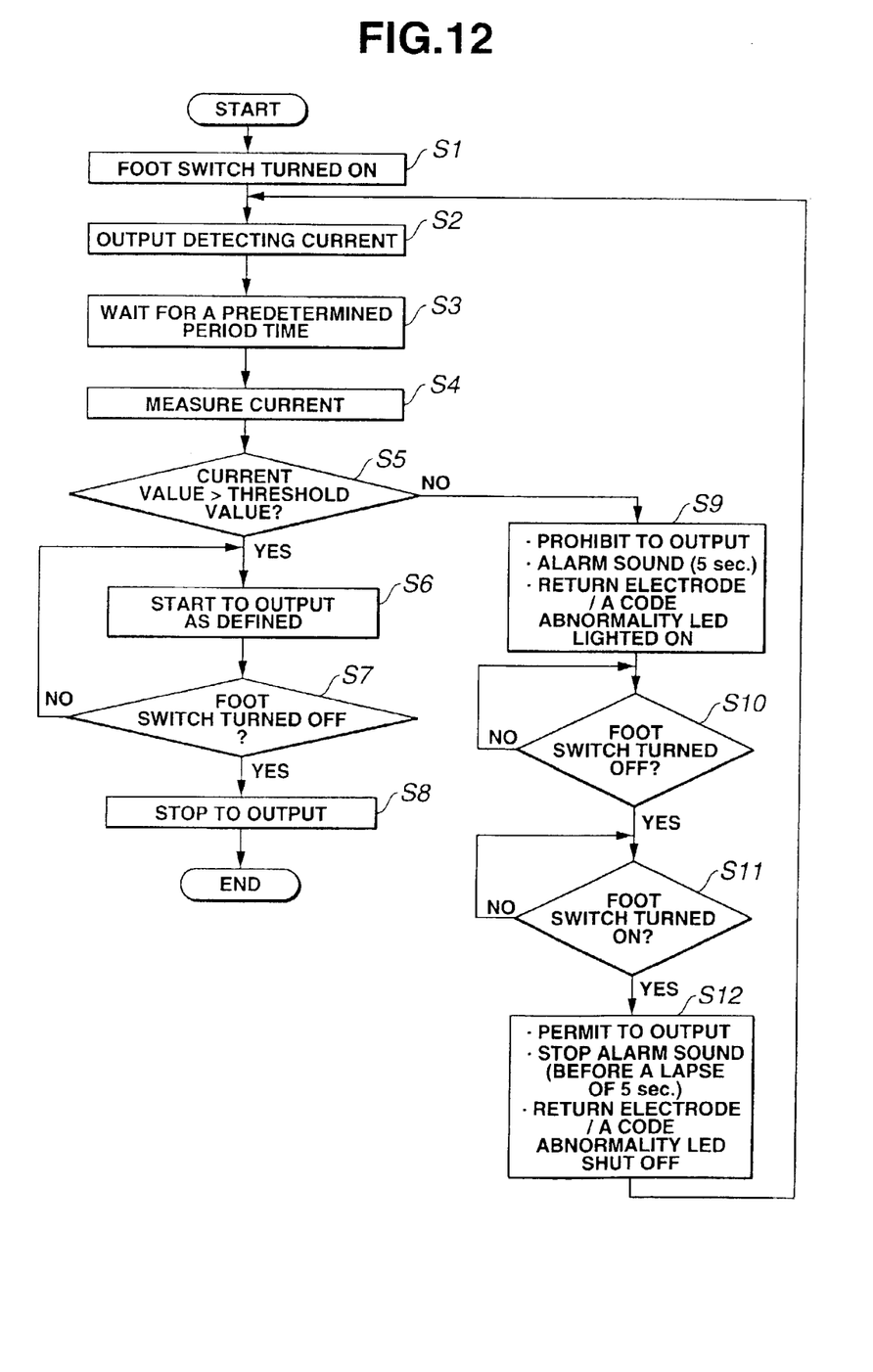
FIG. 12 is a flowchart for explaining an operation of the resectscope apparatus in FIG. 1.
Figure 13:
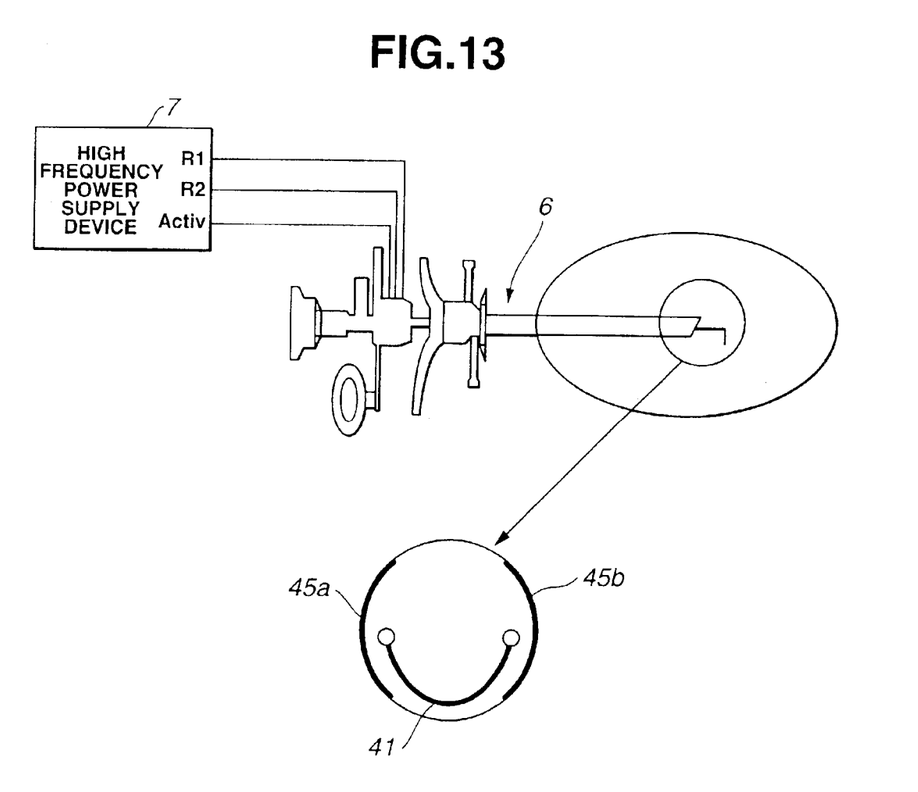
FIG. 13 is a diagram showing a variation of the resectscope apparatus in FIG. 1.
Figure 14:
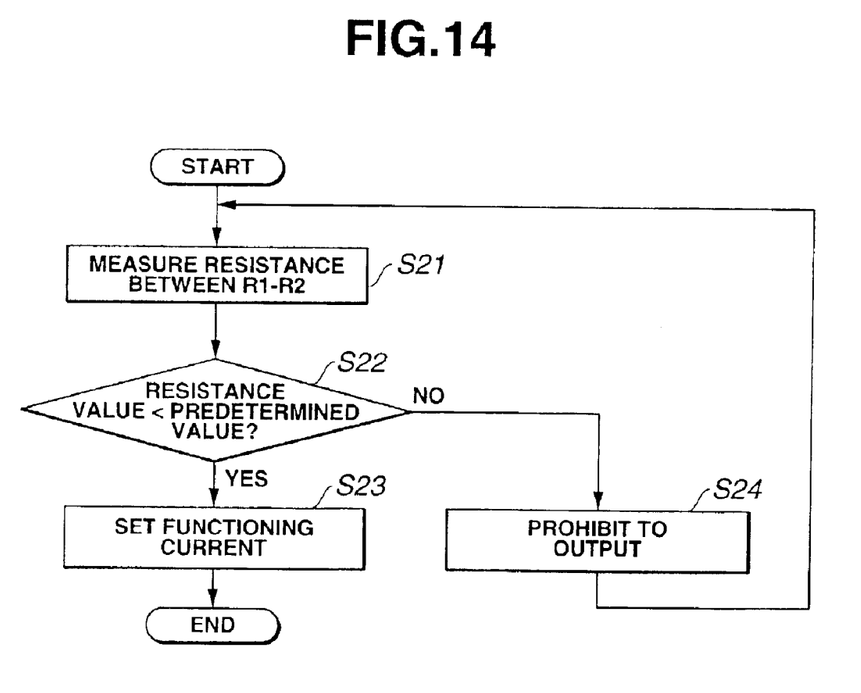
FIG. 14 is a flowchart for explaining an operation of the resectscope apparatus in FIG. 13.

FIGS. 1 to 14 relate to an embodiment of the invention. FIG. 1 is a construction diagram showing a construction of a resectscope apparatus. FIG. 2 is a construction diagram showing a construction of a treating electrode in FIG. 1. FIG. 3 is a construction diagram showing a construction of a high frequency power supply device in FIG. 1. FIG. 4 is a construction diagram showing a construction of a detecting circuit in FIG. 3. FIG. 5 is a first diagram for explaining an operation of a connection detecting circuit in FIG. 4. FIG. 6 is a second diagram for explaining an operation of a connection detecting circuit in FIG. 4. FIG. 7 is a diagram showing load characteristics of power supply in an output transformer circuit in FIG. 3. FIGS. 8(a) and 8(b) are diagrams for explaining an operation of a treating electrode by using power supplied from the output transformer circuit in FIG. 3. FIG. 9 is a diagram showing current flowing between a treating electrode and return electrode in FIG. 1 by using a conductive liquid. FIG. 10 is a diagram showing current flowing between the treating electrode and return electrode in FIG. 1 in an insulative liquid. FIG. 11 is a diagram showing resistances between the treating electrode and return electrode in FIG. 1 in the conductive liquid and the insulative liquid. FIG. 12 is a flowchart for explaining an operation of the resectscope apparatus in FIG. 1. FIG. 13 is a diagram showing a variation of the resectscope apparatus in FIG. 1. FIG. 14 is a flowchart for explaining an operation of the resectscope apparatus in FIG. 13.

As shown in FIG. 1, a resectscope apparatus 1 mainly includes a resectscope 6 and a high frequency power supply device 7. The resectscope 6 includes a hollow sheath 2, a scope 3, an electrode unit 4, a return electrode 45, and a handle portion 5. The hollow sheath 2 has a through-hole. The scope 3 is provided within the hole of the sheath 2 and is used for observing a lesion or the like. The electrode unit 4 includes a treating electrode 41 at the distal end side. The treating electrode 41 is a long and narrow wire-shaped electrode for treating a lesion. The return electrode 45 is provided within the hole at the distal end of the sheath 2. Current output from the treating electrode 41 returns to the return electrode 45. The handle portion 5 is included in an operating portion. The high frequency power supply device 7 is an energizing unit for the treating electrode 41 of the electrode unit 4, which will be described later. Feedback current from the return electrode 45 returns to the high frequency power supply device 7. ON and OFF of power supply from the high frequency power supply device 7 to the treating electrode 41 of the electrode unit 4 is controlled by a foot switch 75 connected to the high frequency power supply device 7.

The sheath 2 includes an inserting portion 21 and a hand-side body portion 22. The inserting portion 21 is inserted into a body cavity through, for example, the urethra.

The hand-side body portion 22 is provided at the rear end of the inserting portion 21. A water-supply end fitting 23 having a cock is provided on the periphery of the hand-side body portion 22. The water supply end fitting 23 supplies, for example, conductive physiological saline as a perfusion fluid to the treating portion.

The scope 3 and the electrode unit 4 lie through the inserting portion 21. A distal end member 24 is provided at the distal end of the inserting portion 21. The distal end member 24 is made of an insulative member such as a rigid resin member.

The scope 3 includes a rigid inserting tube 31 and a hand-side portion 32. The inserting tube 31 is long and narrow and self-contains an observation optical system. The inserting tube 31 lies through the inserting portion 21 and the distal end member 24. The hand-side portion 32 is provided at the proximal end of the inserting tube 31. An eyepiece portion 33 is provided at the proximal end of the hand-side portion 32. An operator uses the eyepiece portion 33 to make visual observations. A light guide connecting portion 34 is provided on the side of the hand side portion 32. A light guide, not shown, is connected to the light guide connecting portion 34 removably for supplying illumination light for observation.

The electrode unit 4 lies through the inserting portion 21. As shown in FIGS. 1 and 2, the electrode unit 4 mainly includes the treating electrode 41, a bifurcated arm member 43, and a long and narrow metal pipe 44. The treating electrode 41 is placed at the distal end side and is a rigid metal member in a loop shape. The bifurcated arm member 43 fixes and holds a positional relationship of the treating electrode 41 with respect to an inserting axis of the scope 3. One end of the arm member 43 on the distal end side has a rigid and transparent hole and bifurcates. The proximal end of the bifurcated arm member 43 is provided at the distal end of the metal pipe 44. An insulating tube, not shown, covers the periphery of the metal pipe 44. The proximal end of the metal pipe 44 exposes at the rear end of the insulating tube as an electrode connecting portion.

The electrode unit 4 is provided within the inserting portion 21 such that the electrode unit 4 can move back and forth. The treating electrode 41 is provided at a distal end portion opening 25 of the sheath 2 retractably.

The treating electrode 41 and the bifurcated arm member 43 are provided at the distal end of the metal pipe 44. A slider 53 is provided at the proximal end of the metal pipe 44. The slider 53 lies through the inserting portion 21 and the hand-side body portion 22 and extends from the proximal end surface of the hand-side body portion 22. The slider 53 will be described later.

The handle portion 5 mainly includes a sheath connecting portion 51, a guide tube 52 and the slider 53. The sheath connecting portion 51 is connected to the hand-side body portion 22 of the sheath 2 removably. The guide tube 52 projects from the rear end surface of the sheath connecting portion 51. The inserting tube 31 lies through the guide tube 52. The slider 53 has a substantial pipe form and is held by the guide tube 52 slidably.

The slider 53 includes an electrode fixing portion 54, a connector 55 for high frequency power supply and a thumb-hook ring 56. The electrode fixing portion 54 electrically connects to the electrode connecting portion at the rear end of the electrode unit 4. A power supply cord 71 extending from the high frequency power supply device 7 is connected to the connector 55 removably. An operator puts his/her thumb through the ring-shaped thumb-hook ring 56.

The slider 53 and the sheath connecting portion 51 are connected through a flat spring 57. In other words, one end of the flat spring 57 is fixed at a finger hook 58 in a lever shape. The finger hook 58 is fixed at the sheath connecting portion 51 integrally. The other end is fixed at the slider 53. Thus, the flat spring 57 always applies a force to the slider 53 toward the eyepiece portion 33 side.

Therefore, by appropriately operating the thumb-hook ring 56 in the slider 53, the slider 53 is manipulated to move back and forth. Then, the treating electrode 41 of the electrode unit 4 moves back and forth to project and retract from the distal end portion opening 25 of the sheath 2.

A feedback current connector 26 is provided on the periphery of the hand-side body portion 22. A feedback current cord 72 extends from the high frequency power supply device 7 and is connected to the feedback current connector 26 removably. The feedback current connector 26 and the return electrode 45 are electrically connected through a lead line 46 indicated by a solid line, for example.

On the other hand, the high frequency power supply connector 55 and the electrode fixing portion 54 are electrically connected through a lead line 61 indicated by a broken line, for example. Thus, when the power supply cord 71 of the high frequency power supply device 7 is connected to the connector 55 for high frequency power supply, the power supply cord 71 is energized with the treating electrode 41 of the electrode unit 4. Then, a lesion can be treated. In this case, leak current can be measured by calculating a difference between values of current supplied to the treating electrode 41 and feedback current.

Furthermore, a slider positioning fixing member 62 is provided at the proximal end of the guide tube 52. The slider positioning fixing member 62 can prevent the slider 53 from falling out from the guide tube 52. Additionally, the hand-side portion 32 of the inserting tube 31 within the guide tube 52 is fixed integrally to the slider positioning fixing member 62.

The power supply cord 71 and the feedback current cord 72 lie through one connecting cable (not shown) and are connected to the high frequency power supply device 7 through a connecting connector, not shown, at the proximal end side of the connecting cable.

As shown in FIG. 3, the high frequency power supply device 7 includes a control circuit 101, a power supply circuit 102, a high frequency generating circuit 103, a waveform circuit 104, an output transformer circuit 105, current sensors 106a and 106b, a sensor signal processing circuit 107 and a detecting circuit 108. The control circuit 101 controls power supply in response to signals from the foot switch 75. The power supply circuit 102 is controlled by the control circuit 101 and generates direct current power. The high frequency generating circuit 103 switches direct current power from the power supply circuit 102 and generates high frequency power. The waveform circuit 104 is controlled by the control circuit 101 and supplies to the high frequency generating circuit 103 waveform signals of high frequency power generated by the high frequency generating circuit 103. The output transformer circuit 105 amplifies high frequency voltage of the high frequency power generated by the high frequency generating circuit 103 and applies between the treating electrode 41 and the return electrode 45. Then, the output transformer circuit 105 supplies high frequency current to the treating electrode 41. Each of the current sensors 106a and 106b detects high frequency current output from the output transformer circuit 105. The sensor signal processing circuit 107 A/D converts current values detected by the current sensors 106a and 106b. The detecting circuit 108 detects a state of the feedback current cord 72 and detects a connection state of the connecting connector, not shown, at the proximal end side of the connecting cable. The control circuit 101 controls the power supply circuit 102 and the waveform circuit 104 based on digitized current data from the sensor signal processing circuit 107 and an output of the detecting circuit 108.

As shown in FIG. 4, in the detecting circuit 108, the return electrode 45 side of the output transformer circuit 105 is divided before the output into two return lines R1 and R2, which are output through a capacitor. The detecting circuit 108 includes a connection detecting circuit 110 and a resistance detecting circuit 113. The connection detecting circuit 110 detects a connection state of a connecting connector (not shown) at the proximal end side of the connecting cable. The resistance detecting circuit 113 measures a resistance of the return electrode 45 by passing current through the divided two return lines R1 and R2 to check disconnection in the two return lines R1 and R2.

Based on a detection result from the connection detecting circuit 110, when the connecting connector (not shown) at the proximal end side of the connecting cable is not connected, the output is prohibited under control of the control circuit 101. The disconnection of one or both of the two return lines R1 and R2 may be determined based on a detection result of the resistance detecting circuit 113 before the apparatus is used or while the apparatus is being used. Then, under control of the control circuit 101, the output is stopped and an alarm indication and an alarm sound are given by an operation panel 109.

As shown in FIGS. 5 and 6, a connecting connector 121 at the proximal end side of the connecting cable is inserted to a connector receiver 123. The connector receiver 123 is provided in an exterior 122 of the high frequency power supply device 7 containing an insulating material. The connector receiver 123 and the exterior of the connecting connector 121 contain a conductive member of metal, for example. When the connecting connector 121 is inserted to the connector receiver 123, the exterior of the connecting connector 121 and the connector receiver 123 are electrically connected. A substantially L-shaped, conductive flat spring 124 is screwed in the inside of the exterior 122 of the high frequency power supply device 7 in the vicinity of the connector receiver 123. The flat spring 124 is covered by an insulative member 125. When the connecting connector 121 is inserted to the connector receiver 123, a depression 126 at the proximal end side of the connecting connector 121 and the flat spring 124 are electrically connected. Then, the connection detecting circuit 110 detects conduction between the connector receiver 123 and the flat spring 124. The connection detecting circuit 110 detects a connection of the connecting connector 121 when the connecting connector 121 is inserted to the connector receiver 123 so that the connector receiver 123 and the flat spring 124 are brought into conduction.

In FIG. 7, the vertical axis indicates power while the horizontal axis indicates resistance. As shown by a load characteristic in FIG. 7, the control circuit 101 controls the power supply circuit 102 and the waveform circuit 104 such that power supply of the output transformer circuit 105 can be maximum at a resistance R1 of the conductive liquid.

By using the power having the load characteristic of the output transformer 105, high frequency current passes through the treating electrode 41 when the treating electrode 41 of the resectscope 6 according to this embodiment is in contact with a living tissue 152 in a conductive liquid 151 as shown in FIG. 8(a). Then, the high frequency current flows between the treating electrode 41 and the return electrode 45, and the treating electrode 41 generates heat. As shown in FIG. 8(b), bubbles 153 are formed from the conductive liquid 151 on the peripheral surface of the treating electrode 41 and cover the treating electrode 41. As a result, interelectrode resistance between the treating electrode 41 and the return electrode 45 increases from the resistance R1 and becomes high resistance to a substantially insulating state. Then, the voltage increases, and discharging occurs between the treating electrode 41 and the living tissue 152. By using the high frequency current from the discharging, the living tissue is resected and is coagulated for treatment.

As shown in FIG. 9, when the resectscope 6 according to this embodiment is used in the conductive liquid 151 such as physiological saline, current flowing from the treating electrode 41 includes current returning from the conductive liquid 151 to the return electrode 45 directly, as indicated by the solid line, and current returning to the return electrode 45 through the living tissue 152 in contact with the treating electrode 41 and through the conductive liquid 151.

As shown in FIG. 10, when the resectscope 6 according to this embodiment is used in the insulative liquid 161 such as D-sorbitol by mistake, current flowing from the treating electrode 41 includes current returning from the insulative liquid 161 to the return electrode 45 directly, as indicated by the broken line, and current returning to the return electrode 45 through the living tissue 152 in contact with the treating electrode 41 and through the insulative liquid 161.

However, as shown in FIG. 11 in which the vertical axis indicates resistance, the resistance values differ between the resistance between the treating electrode 41 and return electrode 45 in the conductive liquid 151 and the resistance between the treating electrode 41 and the return electrode 45 in the insulative liquid 161. In addition, the treating electrode 41 and the return electrode 45 are located closely. Therefore, when the treating electrode 41 and the return electrode 45 are brought into conduction in the insulative liquid 161 by using power, which can be conducted in the conductive liquid 151, the applied voltage increases. Then, an electrical breakdown is produced between the treating electrode and the return electrode 45. As a result, the apparatus may be damaged.

Therefore, according to this embodiment, a predetermined detecting current is fed from the output transformer circuit 105 by using power, which does not produce an electrical breakdown in the insulative liquid 161 or in the air. Then, resistances of the treating electrode 41 and return electrode 45 are detected. Based on the detected resistance values, whether the treating electrode 41 and the return electrode 45 are in the conductive liquid 151, in the insulative liquid 161 or in the air is determined.

In more detail, when a resectscope apparatus 1 according to this embodiment is used for treatment, and when the foot switch 75 is turned ON at the step S1, as shown in FIG. 12, first of all, whether the treating electrode 41 and return electrode 45 are in the conductive liquid 151, in insulative liquid 161 or in the air is determined before the output.

In other words, under control of the control circuit 101, at a step S2, a predetermined detection current is fed from the output transformer circuit 105 by using power, which does not produce an electrical breakdown even in the insulative liquid 161 or in the air. At a step S3, a predetermined lapse of time until the output is stabilized is waited. At a step S4, the sensor signal processing circuit 107 A/D converts and measures current values detected by the current sensors 106a and 106b.

At a step S5, the control circuit 101 compares the measured current data and a predetermined threshold value. If the current data is larger than the predetermined threshold value, that is, if the resistance value is lower than a predetermined value, the treating electrode 41 and the return electrode 45 are determined as being in the conductive liquid 151. Then, the processing goes to a step S6. At the step S6, the output transformer circuit 105 starts to output for treatment by using power as defined in advance. At a step S7, whether or not the foot switch 75 is turned OFF is detected. If the foot switch 75 is still ON, the processing returns to the step S6, where the output transformer circuit 105 continues to output. When OFF of the footswitch 75 is detected, the output is terminated at a step S8. Then, the processing ends.

At the step S5, if the current data is equal to or lower than the predetermined threshold value, that is, if the resistance value is equal to or higher than the predetermined value, the treating electrode 41 and the return electrode 45 are determined as being in the insulative liquid 161 or in the air. The control circuit 101 prohibits the output at a step S9. The control circuit 101 gives an alarm indication and an alarm sound through the operation panel 109. At steps S10 and S11, the foot switch 75 is turned OFF once. The control circuit 101 waits again until the foot switch 75 is turned ON. Then, at a step S12, reset processing is performed where the output is permitted and the alarm indication and alarm sound are stopped. Then, the processing returns to the step S2.

In this way, according to this embodiment, whether the treating electrode 41 and the return electrode 45 are in the conductive liquid 151, in the insulative liquid 161 or in the air is determined before the output. If the treating electrode 41 and the return electrode 45 are in the insulative liquid 161 or in the air, the output is prohibited. Therefore, an electric breakdown is not produced when energization is performed in the air or in a nonconductive liquid by mistake, resulting in an excessively large voltage.

In the above description, detection current is fed between the treating electrode 41 and the return electrode 45, and current values are measured. Then, whether the treating electrode and the return electrode 45 are in the conductive liquid 151, in the insulative liquid 161 or in the air is determined. However, as shown in FIG. 13, the return electrode 45 may be divided into two, and the processing as shown in FIG. 14 may be performed. In other words, the return lines R1 and R2 are connected to two return electrodes 45a and 45b, respectively, at a step S21. The resistance detecting circuit 113 measures resistances of the two return electrodes 45a and 45b. At a step S22, whether the measured resistance values are lower than a predetermined threshold value or not is determined. If the measured resistance value are lower than the predetermined threshold value, the treating electrode 41 and the return electrode 45 are determined as being in the conductive liquid 151. Then, the processing goes to a step S23. At the step S23, a functioning current is set and the processing ends. If the measured resistance value is equal to or larger than the predetermined threshold value, the treating electrode 41 and the return electrode 45 are determined as being in the insulative liquid 161 or in the air. Then, the processing goes to a step S24. At the step S24, the output is prohibited.

In addition to the treating electrode 41 and the return electrode 45, an electrode for resistance detection may be provided separately.

As described above, according to the resectscope apparatus of the present invention, electric characteristics of perfusion fluids are discriminated. Then, the output can be controlled properly.

The embodiment of the invention has been described above. However, the invention is not limited to the above-described embodiment. Apparently, various changes may be made without departing from the spirit of the invention.

INDUSTRIAL APPLICABILITY

According to the present invention as described above, the resectscope apparatus can be provided, which can control the output properly by discriminating electrical characteristics of perfusion fluids.

What is claimed is:

1. A resectscope apparatus comprising:
   an electrode unit having one of a treating and return electrodes;
   a sheath for housing the electrode unit, the sheath having the other of the treating and return electrodes, the treating and return electrodes adapted to be provided in a conductive solution within a body cavity;
   high frequency current supply means for supplying high frequency current between the treating and return electrodes, in which the high frequency current is discharged from the treating electrode to a living tissue, and the living tissue is resected and is coagulated;
   comparing means for comparing resistance values around the treating and return electrodes with a predetermined threshold value, the predetermined threshold value being set higher than a resistance value in a condition that the treating and return electrodes are in a conductive liquid and lower than a resistance value in a condition that the treating and return electrodes are in an insulative liquid or in air; and
   control means for controlling an output of the high frequency current supply means to the treating electrode based on a comparison result by the comparing means.

2. A resectscope apparatus according to claim 1, further comprising measuring means for measuring a resistance value between the treating and return electrodes, wherein the comparing means compares a measured resistance value and the predetermined threshold value.

3. A resectscope apparatus according to claim 1, wherein at least one of the treating and return electrodes comprises first and second electrodes.

4. A resectscope apparatus according to claim 1, further comprising an electrode for detection in the vicinity of the treating and return electrodes separately from the treating and return electrodes; and measuring means for measuring a resistance value between the electrode for detection and at least one of the treating and return electrodes, wherein the comparing means compares a measured resistance value and the predetermined threshold value.

5. A resectscope apparatus according to claim 1, further comprising a pair of electrodes for detection separately from the treating and return electrodes in the vicinity of the treating and return electrodes; and measuring means for measuring a resistance value between the pair of electrodes for detection, wherein the comparing means compares a measured resistance value and the predetermined threshold value.

6. A resectscope apparatus comprising:
   treating and return electrodes, the treating and return electrodes adapted to be provided in a conductive solution within a body cavity;
   high frequency current supply means for supplying high frequency current between the treating and return electrodes, in which the high frequency current is discharged and the living tissue is resected and is coagulated;
   determining means for determining a type of the conductive solution based on resistance values around the treating and return electrodes, the determining means having a predetermined threshold value to be compared with the resistance values around the treating and return electrodes, the predetermined threshold value being set higher than a resistance value in a condition that the treating and return electrodes are in an insulative liquid or in air; and
   control means for controlling an output of the high frequency current supply means to the treating electrode based on the type of conduction solution determined by the determining means.

7. A resectscope apparatus comprising:
   an electrode unit having one of treating and return electrodes;
   a sheath for housing the electrode unit, the sheath having the other of the treating and return electrodes, the treating and return electrodes adapted to be provided in a conductive solution within a body cavity;
   high frequency current supply device, electrically connected with the treating and return electrodes, for supplying high frequency current between the treating and return electrodes, in which the high frequency current is discharged from the treating electrode to a living tissue, and the living tissue is resected and is coagulated;
   resistance detecting device, electrically connected with the treating and return electrodes, for detecting resistance values around the treating and return electrodes, the resistance values being compared with a predetermined threshold value, the predetermined threshold value being set higher than a resistance value in a condition that the treating and return electrodes are in a conductive liquid and lower than a resistance value in a condition that the treating and return electrodes are in an insulative liquid or in air; and
   control device, electrically connected with the treating and return electrodes, and the high frequency current supply device, for controlling an output of the high frequency current supply device to the treating electrode based on a comparison result by the resistance detecting circuit.

8. A resectscope apparatus according to claim 7, wherein the resistance detecting device comprises a measuring device for measuring a resistance value between the treating and return electrodes, wherein the measured resistance value is compared with the predetermined threshold value.

9. A resectscope apparatus according to claim 7, wherein at least one of the treating and return electrodes comprises first and second electrodes.

10. A resectscope apparatus according to claim 7, further comprising an electrode for detection in the vicinity of the treating and return electrodes separately from the treating and return electrodes; and a measuring device for measuring a resistance value between the electrode for detection and at least one of the treating and return electrodes, wherein the measured resistance value is compared with the predetermined threshold value.

11. A resectscope apparatus according to claim 7, further comprising a pair of electrodes for detection separately from the treating and return electrodes in the vicinity of the treating and return electrodes; and a measuring device for measuring a resistance value between the pair of electrodes for detection, wherein the measured resistance value is compared with the predetermined threshold value.

12. A resectscope apparatus according to claim 1, wherein the high frequency current supply means comprises a connection detection circuit that detects a connection state of a connection cable connected with the return electrode, wherein the control means prohibits the supply of high frequency current when the connection detecting circuit detects a state of disconnection of the connecting cable.

13. A resectscope apparatus according to claim 6, wherein the high frequency current supply means comprises a connection detecting circuit that detects a connection state of a connecting cable connected with the return electrode, wherein the control means prohibits the supply of high frequency current when the connection detecting circuit detects a state of disconnection of the connecting cable.

14. A resectscope apparatus according to claim 7, wherein the high frequency current supply device comprises a connection detecting circuit that detects a connection state of a connecting cable connected with the return electrode, wherein the control device prohibits the supply of high frequency current when the connection detecting circuit detects a state of disconnection of the connecting cable.

* * * * *